United States Patent [19]

Coombs

[11] Patent Number: 4,839,356

[45] Date of Patent: Jun. 13, 1989

[54] THIAZINONE DERIVATIVES

[75] Inventor: Mandy E. Coombs, Kent, United Kingdom

[73] Assignee: Shell Internationale Research Maatschappij B.V., The Hague, Netherlands

[21] Appl. No.: 49,247

[22] Filed: May 13, 1987

[51] Int. Cl.[4] .................... C07D 279/06; A61K 31/54
[52] U.S. Cl. ................................. 514/227.2; 544/54; 544/55
[58] Field of Search .......................... 544/54; 514/226

[56] References Cited

FOREIGN PATENT DOCUMENTS 108541 9/1974 Fed. Rep. of Germany .

OTHER PUBLICATIONS

Justus Liebigs, Ann. Chem., 77, (8), pp. 1249–1266, (1977).

Rozhkova et al., CA 94: 78267 C.
Solyom et al., CA 75: 5845N.
Sineokov et al., CA 68: 5913 b.

Primary Examiner—Jane T. Fan

[57] ABSTRACT

The invention provides thiazinone derivatives of general formula I:

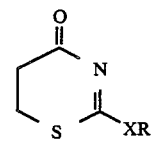

wherein X is O, S or NH, and R represents an optionally substituted alkyl, alkenyl, heterocyclic or aryl group; a process for the preparation of such compounds; compositions containing them and their use as fungicides.

6 Claims, No Drawings

THIAZINONE DERIVATIVES

This invention relates to thiazinone derivatives, a process for the preparation of such compounds, compositions containing them, and to their use as fungicides.

According to the invention there is provided a thiazinone compound of the general formula I:

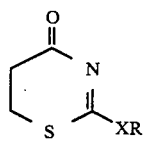

wherein X represents an oxygen or sulphur atom or the group NH, and R represents an optionally substituted alkyl, alkenyl, heterocyclic or aryl, preferably phenyl or naphthyl, group.

When any of the foregoing substituents are designated as being optionally substituted, the substituent groups which are optionally present may be any one or more of those customarily employed in the development of pesticidal compounds, and/or the modification of such compounds to influence their structure/activity, persistence, penetration or other property. Specific examples of such substituents include halogen, especially fluorine, chlorine or bromine, atoms, and nitro, cyano, amino, hydroxyl, carboxyl, alkyl, haloalkyl, especially trifluoromethyl, cycloalkyl, optionally substituted phenyl, alkanoyl, alkoxy, optionally substituted phenoxy, alkylthio, alkylsulphinyl, alkylsulphonyl, carbamoyl, alkylamido and imidazolyl groups, or in the case where R represents a phenyl group, that phenyl group may be vicinyl disubstituted by a heterocyclic ring such as thiadiazole. When any of the foregoing substituents represents or contains an alkyl or alkenyl substituent group, this may be linear or branched and may contain up to 12, preferably up to 6, and especially up to 4, carbon atoms, suitable examples being methyl, ethyl, propyl and propenyl. When they represent a cycloalkyl group this may contain from 3 to 8, carbon atoms, and is suitably cyclohexyl. When they represent an aryl group, this is suitably phenyl or naphthyl, and suitable heterocyclic groups are pyridyl, pyrimidinyl, pyrazinyl, quinolyl, indolyl, benzimidazolyl, benzoxazolyl or coumarinyl groups, which may be present as the N-oxides.

Preferably X represents an oxygen or sulphur atom. It is also preferred that R represents a phenyl group substituted by 1 or 2 substituents selected from chlorine atoms, methyl groups and trifluoromethyl groups.

The invention also provides a process for the preparation of a thiazinone compound of formula I as defined above which comprises reacting a compound of the general formula II

wherein Hal represents a halogen atom, with a compound of the general formula III

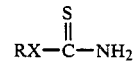

wherein X and R are as defined above. The reaction is conveniently carried out in an inert organic solvent, such as acetone at reflux temperature. Preferably it is carried out in the presence of a base, suitably an organic base such as a trialkylamine, triethylamine being most preferred.

The starting compound of formula III, that is, the thiocarbamate compound, may be conveniently prepared by reacting a compound of formula RXCN in which R and X are as defined above with hydrogen sulphide, suitably in an organic solvent such as dimethyl formamide, ethanol or ether.

In another aspect, the invention provides a fungicidal composition which comprises a carrier and, as active ingredient, a thiazinone compound of formula I as defined above; and also a method of making such a composition which comprises bringing a compound of formula I into association with at least one carrier.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur, natural and synthetic resins, for example coumarone resins, polyvinyl chloride, and styrene polymers and copolymers; solid polychlorophenols; bitumen; waxes; and solid fertilisers, for exampler superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. This preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing 1/2–10% w of active ingredient. Granules are usually prepared to have a size between 10 and 100 BS mesh (1.676 0.152 mm), and may be manufactured by agglomeration or impregnation techniques. Generally, granules will contain 1/2–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing herbicidal, insecticidal or fungicidal properties.

Of particular interest in enhancing the duration of the protectant activity of the compounds of this invention is the use of a carrier which will provide a slow release of the fungicidal compounds into the environment of the plant which is to be protected. Such slow-release formulations could, for example, be inserted in the soil adjaccent to the roots of a vine plant, or could include an adhesive compoment enabling them to be applied directly to the stem of a vine plant.

The invention still further provides the use as fungicide of a thiazinone compound of the general formula I as defined above, and a method for combating fungus at a locus, which comprises treating the locus, which may be for example be plants subject to or subjected to fungal attack, seeds of such plants or the medium in which such plants are growing or are to be grown, with such a compound.

The present invention is of wide applicability in the protection of crop plants against fungal attack. Typical crops which may be protected include vines, grain crops such as wheat and barley, rice, beans and applies. The duration of protection is normally dependent on the individual compound selected, and also a variety of external factors, such as climate, whose impact is normally mitigated by the use of a suitable formulation.

The invention is illustrated in the following Examples.

EXAMPLE 1

(A) Preparation of O-(4-chloro-2-methyl)phenyl thiocarbamate

Hydrogen sulphide gas was passed through a solution of 4-chloro-2-methylphenyl cyanate (4g 0.024mol) in dry dimethyl formamide (30ml) for 2 hours. The mixture was stirred overnight, then water (30 ml) was added. The solution was extracted with dichloromethane (60ml), and the organic layer was dried over magnesium sulphate. Concentration by rotary evaporation gave an orange oil. This was purified by flash chromatography, using 25:75 ethylacetate: petrol, to yield the desired product as a white solid, m.pt. 150° C.

| Analysis | | | |
|---|---|---|---|
| Calculated: | C 47.6; | H 4.0; | N 6.9% |
| Found: | C 47.5; | H 4.0; | N 6.5% |

(B) Preparation of 2-(4-chloro-2-methyl)phenoxy-5,6-dihydrothiazinone

Triethylamine (1ml. 0.007 mol) was added to a solution of the O-(4-chloro-2-methyl)phenyl thiocarbamate obtained in A (1.5g, 0.007 mol) and acryloyl chloride (0.62 ml, 0.007 mol) in acetone (20ml). The resulting solution was refluxed for 24 hours. After cooling the acetone was removed by rotary evaporation and the residue taken up in dichloromethane and then washed with water. The organic layer was dried over magnesium sulphate and then concentrated by rotary evaporation. The residue was purified by flash chromatography using 25:75 ethyl acetate: petrol to yield the desired final product, m.pt. 128° C.

| Analysis | | | |
|---|---|---|---|
| Calculated: | C 51.7; | H 3.9; | N 5.5% |
| Found: | C 51.4; | H 4.0; | N 5.8% |

EXAMPLE 2

2-(4-trifluoromethyl)phenoxy-5,6-dihydrothiazinone was prepared by procedures similar to those described in Example 1 above.

| Analysis | | | |
|---|---|---|---|
| Calculated: | C 48.0; | H 2.9; | N 5.1% |
| Found: | C 47.9; | H 3.2; | N 5.9% |

EXAMPLE 3

The fungicidal activity of compounds of the invention was determined by means of the following tests.

(a) Antisporulant activity against vine downy mildew (Plasmopara viticola; P.v.a)

The test is a direct antisporulant one using a foliar spray. The lower surfaces of leaves of whole vine plants (cv Cabernet Sauvignon) are inoculated by spraying with an aqueous suspension containing $10^4$ zoosporangia/ml 2 days prior to treatment with the test compound. The inoculated plants are kept for 24 hours in a high humidity compartment, and then 24 hours at glasshouse ambient temperature and humidity. Infected leaves are sprayed on their lower surfaces with a solution of active material in 1:1 water/acetone containing 0.04% "TWEEN" 20 (Trade Mark; a polyoxyethylene sorbitan ester surfactant). The spraying is carried out with a moving track sprayer giving an application rate of 1kg/ha. After spraying, the plants are returned to normal glasshouse conditions for 96 hours and are then transferred to the high humidity compartment for 24 hours to induce sporulation, prior to assessment. is based on the percentage of the leaf area covered by sporulation compared with that on control leaves.

(c) Direct protectant activity against vine downy mildew (Plasmopara viticola; P.v.p)

The test is a direct protectant one using a foliar spray. The lower surfaces of leaves of whole vine plants (cv Cabernet Sauvignon) are sprayed with the test compound at a dosage of 1 kilogram of active material per hectare using a track sprayer as described under (a), and after a subsequent 24 hours under normal glasshouse conditions the lower surfaces of the leaves are inoculated by spraying with an aqueous solution containing $10^4$ zoosporangia/ml. The inoculated plants are kept for 24 hours in a high humidity compartment, 5 days under normal glasshouse conditions and then returned for a further 24 hours to high humidity. Assessement is based on the percentage of leaf area covered by sporulation compared with that on control leaves.

(d) Direct protectant activity against vine grey mould (Botrytis cinerea; Bcp)

The test is a direct protectant one using a foliar spray. The lower surfaces of detached vine leaves (cv Cabernet Sauvignon) are sprayed with the test compound at a dosage of 1kg/ha using a track sprayer as in (a). 24 Hours after spraying the leaves are inoculated with droplets of aqueous suspension containing $10^5$ conidia/ml. After a further 5 days in high humidity the percentage of leaf area covered by disease is assessed.

(e) Activity against wheat leafspot (Leptosphaeria nodorum; Ln.)

The test is a direct therapeutic one, using a foliar spray. Leaves of wheat plants (cv Mardler), at the single leaf stage, are inoculated by spraying with an aqueous suspension containing $1 \times 10^6$ spores/ml. The inoculated plants are kept for 24 hours in a high humidity compartment prior to treatment. The plants are sprayed with a solution of the test compound at a dosage of 1 kilogram of active material per hectare using a track sprayer as described under (a). After drying, the plants are kept for 6–8 days at 20–25° C. and moderate humidity, followed by assessment. Assessment is based on the density of lesions per leaf compared with that on leaves of control plants.

(f) Activity against barley powdery mildew (Erysiphe graminis f.sp. hordei; Eg)

The test is a direct therapeutic one, using a foliar spray. Leaves of barley seedlings, (cv. Golden Promise) are inoculated by dusting with mildew conidia one day prior to treatment with the test compound. The inoculated plants are kept overnight at glasshouse ambient temperature and humidity prior to treatment. The plants are sprayed with the test compound at a dosage of 1 kilogram of active material per hectare using a track sprayer as described under (a). After drying, plants are returned to a compartment at 20°–25° C. and moderate humidity for up to 7 days, followed by assessment. Assessment is based on the percentage of leaf area covered by sporulation compared with that on leaves of control plants.

(g) Activity against apple powdery mildew (Podosphaera leucotricha; Pl)

The test is a direct therapeutic one using a foliar spray. The upper surfaces of leaves of apple seedlings are inoculated by spraying with an aqueous suspension containing $10^5$ conidia/ml 2 days prior to treatment with the test compounds. The inoculated plants are immediately dried and kept at glasshouse ambient temperatures and humidity prior to treatment. The plants are sprayed with the test compound at a dosage of 1 kilogram of active material per hectare using a track sprayer as described under (a). After drying the plants are returned to a compartment at 20°-25° C. and moderate humidity for up to 9 days, followed by assessment. Assessment is based on the percentage of the leaf area covered by sporulation compared with that on leaves of control plants.

(h) Activity against broad bean rust (Uromyces fabae Uf)

The test is a therapeutic one using a foliar spray. Pots containing 1 plant per pot are inoculated by spraying an aqueous suspension, containing $5 \times 10^4$ spores/ml plus a little "Tween 20" (Trade Mark), onto the upper surface of each leaf 20-24 hours before treatment with test compound. The inoculated plants were kept overnight in a high humidity compartment, dried at glasshouse ambient temperature and then sprayed, on the leaf upper surface, with the test compound at a dosage of 1 kilogram of active material per hectare using a track sprayer as described under (a). After treatment the plants were kept at glasshouse temperature and assessment made 11-14 days after treatment. Symptoms are assessed on the relative density of sporulating pustules per plant compared with that on control plants.

(i) Activity against rice leaf blast (Pyricularia oryzae Po)

The test is a direct therapeutic one using a foliar spray. The leaves of rice seedlings (about 30 seedlings per pot) are sprayed with an aqueous suspension containing $10^5$ spores/ml 20-24 hours prior to treatment with the test compound. The inoculated plants are kept overnight in high humidity and then allowed to dry before spraying with the test compound at a dosage of 1 kilogram of active material per hectare using a track sprayer as described under (a). After treatment the plants are kept in a rice compartment at 25-30° C. and high humidity. Assessments are made 4-5 days after treatment and are based on the density of necrotic lesions per leaf when compared with control plants.

(j) Activity against tomato early blight (Alternaria solani; As)

This test measures the contact prophylactic activity of test compounds applied as a foliar spray. seedlings (cv Outdoor Girl) are grown to the at which the second true leaf is expanded. The are treated using a track sprayer as described under (a). Test compounds are applied as solutions or suspensions in a mixture of acetone and water (50:50v/v) containing 0.04% surfactant ("TWEEN 20"- Trademark).

One day after treatment the seedlings are inoculated by spraying the leaf upper surfaces with a suspension of A. solani conidia containing $10^4$ spores/ml. For 3 days after inoculation plants are kept moist in a glasshouse compartment at or near 100% RH and 21° C. Thereafter plants are kept under humid, but not saturated, conditions.

Disease is assessed 7 days after inoculation, based on the density and spread of lesions.

k) Activity against wheat eyespot in-vitro (Pseudocercosporella herpotrichoides; PhI)

This test measures the in vitro activity of compounds against the fungus causing wheat eyespot.

The Test Compound is dissolved or suspended in acetone and is added to molten half strength Potato Dextrose Agar to give a final concentration of 100ppm compound and 3.5% acetone. After agar has set, plates are inoculated with 6 mm diameter plugs of agar/mycelium taken from a 14 day old culture of P. herpotrichoides.

Plates are incubated at 20° C. for 12 days and radial growth from the inoculation plug is measured.

(l) Activity against Fusarium in-vitro (Fusarium species; FsI)

This test measures the in vitro activity of compounds against a species of Fusarium that causes stem and root rots.

Compound is dissolved or suspended in acetone and added to molten half strength Potato Dextrose Agar to give a final concentration of 100ppm compound and 3.5% acetone. After agar has set, plates are inoculated with 6mm diameter plugs of agar and mycelium taken from a 7 day old culture of Fusarium sp.

Plates are incubated at 20° C. for 5 days and radial growth from the plug is measured. The extent of disease control in all the above tests is expressed as a rating compared with either an untreated control or a diluent-sprayed-control, according to the criteria:

0 = less than 50% disease control
1 = about 50-80% disease control
2 = greater than 8-% disease control The results of these tests are set out in Table II below.

TABLE II

| Example No. | Fungicidal Evaluation |
|---|---|
| 1 | Pvp 1; Ph 2; Fs 2 |
| 2 | Pvp 1; Ph 2; Fs 1 |

I claim:

1. A thiazinone compound of formula

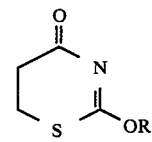

wherein R represents a phenyl group substituted by 1 or 2 substituents selected from the group of consisting of chlorine atoms, methyl groups and trifluoromethyl groups.

2. A compound as claimed in claim 1 wherein R represents a 4-chloro-2-methylphenyl group or a 4-trifluoromethylphenyl group.

3. A fungicidal composition which comprises a carrier together with, as active ingredient a fungicidally effective amount of a thiazinone compound as claimed in claim 1.

4. A composition as claimed in claim 3 which comprises at least two carriers, at least one of which is a surface-active agent.

5. A method of combating fungus at a locus which comprises treating the locus with a fungicidally effective amount of a compound as claimed in claim 1 or a composition as claimed in claim 8.

6. A method as claimed in claim 5, wherein the locus comprises plants subject to or subjected to fungal attack, seeds of such plants, or the medium in which the plants are growing or are to be grown.

* * * * *

UNITED STATES PATENT AND TRADEMARK OFFICE
CERTIFICATE OF CORRECTION

PATENT NO. : 4,839,356

DATED : June 13, 1989

INVENTOR(S) : Mandy E. Coombs

It is certified that error appears in the above-identified patent and that said Letters Patent is hereby corrected as shown below:

On the cover page under "FOREIGN PATENT DOCUMENTS", "Fed. Rep. of Germany" should be -- German Democratic Republic --

On the cover page under "Other Publications," "5913b" should be -- 59513b --.

Claim 5 (column 10, line 2), "8" should be -- 3 --.

Signed and Sealed this

Thirteenth Day of March, 1990

Attest:

JEFFREY M. SAMUELS

*Attesting Officer*  *Acting Commissioner of Patents and Trademarks*